United States Patent [19]

Selner et al.

[11] Patent Number: 4,753,228

[45] Date of Patent: Jun. 28, 1988

[54] APPARATUS FOR FOOT STABILIZATION

[76] Inventors: Allen J. Selner; Marc D. Selner, both of 4918 Libbit Ave., Encino, Calif. 91436

[21] Appl. No.: 885,303

[22] Filed: Jul. 14, 1986

[51] Int. Cl.$^4$ ............................................... A61F 5/00
[52] U.S. Cl. ..................... 128/80 R; 36/89; 128/80 D; 128/80 G; 128/166.5
[58] Field of Search ............... 128/80 R, 80 C, 80 D, 128/80 A, 80 G, 166, 166.5; 36/89, 91, 58.5

[56] References Cited

U.S. PATENT DOCUMENTS

| | | | |
|---|---|---|---|
| 1,156,621 | 10/1915 | O'Dwyer | 128/166.5 |
| 1,283,335 | 10/1918 | Shillcock | 128/611 |
| 1,365,512 | 1/1921 | Lewis | 128/166.5 |
| 1,443,844 | 1/1923 | Jensen | 128/166 |
| 1,462,534 | 7/1923 | Condylis et al. | 128/166.5 |
| 1,465,970 | 8/1923 | Cleveland et al. | 128/166 |
| 1,788,852 | 1/1931 | Arthur | 128/166.5 |
| 2,292,643 | 8/1942 | Layana | 128/166.5 |
| 2,358,966 | 9/1944 | Einstoss | 128/166.5 |
| 2,708,930 | 5/1955 | Lowman | 128/80 D |
| 3,073,305 | 1/1963 | Biggs, Jr. et al. | 128/80 H X |
| 4,313,433 | 2/1982 | Cramer | 128/80 H |
| 4,367,733 | 1/1983 | Stromgren | 128/166 |
| 4,392,487 | 7/1983 | Selner et al. | 128/80 H |
| 4,495,942 | 1/1985 | Palumbo | 128/80 H |

Primary Examiner—Edgar S. Burr
Assistant Examiner—Moshe I. Cohen
Attorney, Agent, or Firm—Pretty, Schroeder, Brueggemann & Clark

[57] ABSTRACT

Improved apparatus for stabilizing the foot to control gait, wherein a sleeve and a strap of limited elasticities are wrapped around the foot in a prescribed manner with the strap ends attached to the sleeve so as to limit excessive pronation, assist in resupination and enhance retrograde stability to the major joints of the foot. The sleeve is slid over the foot and around the arch. The strap extends at an angle from a location on the sleeve adjacent to the bottom of the foot, up across the instep, over the top of the foot, around the heel, back along the medial side of the foot and fastens to the sleeve at an adjustable location below the first metatarsal of the foot. The strap is adjustably and releasably connected at intermediate locations to the sleeve.

19 Claims, 1 Drawing Sheet

APPARATUS FOR FOOT STABILIZATION

BACKGROUND OF THE INVENTION

This invention relates generally to orthopedic devices for the feet, and relates more specifically to an improved foot stabilization apparatus for controlling gait by limiting excessive pronation and assisting in resupination of the foot during walking or running. A related apparatus and method is disclosed in U.S. Pat. No. 4,392,487 issued to Applicants.

A normal human gait cycle consists of three phases: the contact phase in which the heel alone initially makes contact with the ground, the mid-stance phase in which the entire sole or plantar surface of the foot is in contact with the ground, and the propulsive phase wherein the balls of the foot and the toes push off. During the gait cycle, the foot and ankle tend naturally first to undergo movement known as pronation and then to move in a manner known as supination. While these movements of the foot and ankle are complex and can only be accurately described with reference to the three conventional anatomical planes (i.e., the sagittal, frontal and transverse planes), in simple terms pronation is an inward rolling and supination is an outward rolling of the foot and ankle.

More specifically, pronation and supination of the foot and ankle are a function primarily of the subtalar joint and the midtarsal joints. The subtalar joint is defined as the articulation between the talus and calcaneus (heel) bones. The midtarsal joints comprise the calcaneal-cuboid joint, which is defined as the articulation of the calcaneus and cuboid bones, and the talar-navicular joint, which is defined as the articulation of the talus (ankle) and the navicular bones. The navicular bone forms part of the arch structure.

A certain amount of pronation of the foot during walking or running is desirable. Generally speaking, pronation occurs during the contact phase and about the first half of the mid-stance phase of a normal gait cycle. In the pronated position, the bones of the foot tend to become mobile or loose relative to one another, allowing the plantar surface to adapt to possibly uneven terrain. During the last half of the mid-stance phase and during the propulsive phase, however, resupination is essential so that the bones of the foot become relatively stable or locked to enable one to push-off.

Although some pronation is normal, many persons are troubled by excessive pronation in which the foot and ankle roll too far inwardly and the bones of the foot become hypermobile relative to one another. The combination of excessive pronation and resupination during a gait cycle can result in exaggerated back and forth rotational movement of the leg and knee with accompanying results that are highly undesirable. For example, various forms of muscular fatigue in children (sometimes called "growing pains") and in adults (such as back pain and leg fatigue) have been traced to excessive pronation. Likewise, excessive pronation has been found to be a cause of arch strain, heel pain, pain in the knee joint and the patella (knee cap), and foot deformities such as bunions and hammer toes (which in turn can result in corns and calluses). The effects of excessive pronation are particularly a problem for athletes, including those who run or jog.

Various attempts have been made by the prior art to lessen or eliminate the effects of excessive pronation. The most commonly attempted solution has been use of conventional arch support wedges. This approach is believed motivated by the fact that pronation is accompanied by a general stretching and flattening of the arch, and persons with flattened arches tend to suffer more frequently from the effects of excessive pronation. However, use of arch support wedges has been found to be a generally ineffective solution that is directed to a symptom rather than the source of the problem. Some persons have flattened arches and do not excessively pronate, while other persons with raised arches suffer greatly from the effects of excessive pronation. Excessive pronation does not result from flattened arches, but rather is primarily the result of the internal structure of the foot and ankle, and in particular the motions of the subtalar and midtarsal joints. It is also influenced by external forces generated by knock-kneed, pigeon-toed or duck walking, for instance. Arch support wedges cannot control these factors, particularly in a person with naturally high arches, and even feet characterized by flattened arches will tend to roll over conventional arch support wedges. Moreover, arch support wedges require shoes and thus are impractical for certain athletes such as dancers.

Another approach to the problem has been to carefully wrap adhesive tape circularly around the arch and to connect it with tape extending rearwardly along each side of the foot and around the heel. The tape extending around the heel serves to maintain the circular portion in position and to act as a lateral restraint on foot motion thereby preventing excessive pronation. A further and highly significant advantage of tape over arch support and orthotics is in its ability to apply forces of the major foot joints against each other, providing a holding effect or enhanced retrograde stability unobtainable with any device that fits under the foot. To be effective, however, the tape must be applied very carefully in a prescribed manner by a qualified professional. Thus, this solution is not adapted for ordinary self-application. Also, tape has the disadvantage of stretching after a short time and any particular taping can last at most a few days. Further, the direction of pull and pressure cannot be adjusted after wrapping. In addition, tape does not assist in resupination of the foot. Tape also is irritating and cannot be used over.

Hence, those concerned with the development and use of orthopedic devices for the foot have long recognized the need for more effective devices, which are capable of self-application, for alleviating the problems caused by excessive pronation, and which will assist in resupination and provide enhanced retrograde stability approaching that of tape. A method and apparatus directed at these objectives is disclosed in the aforementioned U.S. Pat. No. 4,392,487. A sleeve and a connecting strap are wrapped around the foot in a prescribed fashion with the strap ends anchored to the sleeve. The sleeve is formed of a relatively elongate sheet of material and is elastic in the circumferential direction but is substantially inelastic in the lateral direction, with the opposite ends of the sheet adapted to be releasably joined together for adjustability. The strap is relatively narrow and elongate, and is formed of a material that is substantially inelastic in the longitudinal direction.

The sleeve is wrapped snugly around the arch of the foot with the ends of the sleeve joined together. The strap is wrapped from a location on the sleeve adjacent to the bottom of the foot, up across the instep, over the top of the foot and around the heel, from which position the strap is wrapped back to the sleeve and fastens thereto through an attachment loop near the instep. The strap is then tightened with the foot aligned in a preferred position (turned inwardly and rolled slightly medially upward). The substantial inelasticity of the strap and the fact that the sleeve is locked around the foot with both ends of the strap anchored to the sleeve on the medial side of the foot, all contribute to restraining the foot from excessive pronation and assisting in resupination during walking or running.

Use of such a foot stabilization apparatus has been found to be a generally effective solution. However, experience has taught that certain improvements in comfort, elasticity, restraint and holding effect are desirable. Among other things, for example, the anchor point of the releasably attachable end of the strap is fixed at a location rendering the strap substantially parallel to the forces exerted on the foot by walking or running and, therefore, the strap is not as efficient as it might be in restraining those forces and providing the desired holding effect. The substantial inelasticity of the sleeve in the lateral direction limits its ability to most comfortably conform to the shape of the foot. Further, adequate tightening of the inelastic strap to restrain excessive pronation can cause uncomfortable and unnecessary tension in the arch.

Accordingly, those concerned with the development and use of orthopedic devices for the foot have recognized the need for further improvement in the foregoing areas. The present invention fulfills the desire for these and other related improvements.

SUMMARY OF THE INVENTION

Briefly, and in general terms, the present invention provides a new and improved apparatus for stabilizing movement of the foot to control gait by which the foot is more effectively restrained from excessively pronating, while providing both greater holding effect and assistance in resupination, along with increased comfort to the wearer.

Basically, the present invention provides such a superior apparatus for stabilizing the foot by means of an improved sleeve and strap arrangement. More specifically, the sleeve is formed of two thin and flexible portions adjoining one another end-to-end around the circumference of the sleeve. The first sleeve portion is of an extent to engage the plantar and arch portions of the foot, and the second sleeve portion is of an extent to engage the instep. The first sleeve portion has limited elasticity in both the circumferential and lateral directions for conformance to the foot, while remaining sufficiently inelastic to help apply holding forces for retrograde stability. The second sleeve portion has similar limited elasticity in the circumferential direction, again for conformance to the foot and so as not to overly restrict movement of the metatarsal bones, while also helping to apply holding forces. The second sleeve portion is substantially inelastic in the lateral direction so that, in conjunction with gripping means lining the inside of the sleeve, it provides a stable base from which restraining forces can be applied by the strap, as will be described.

The strap is sufficiently long to extend from its first end, which is connected to the first sleeve portion at about the lateral plantar location on the foot, toward and over the arch, across the instep, around the heel and back to the arch region where means are provided for adjustably and releasably fastening the second end of the strap. Preferably, and significantly, the second end of the strap may be fastened selectively to the sleeve or back onto the strap itself below the first metatarsal of the foot, so that the restraining forces exerted by the strap are transverse rather than parallel to the forces exerted on the foot by walking or running which lead to excessive pronation. The resulting increased restraining force is sufficiently great that the strap may have limited elasticity for improved comfort and greater assistance in resupination and still exert adequate restraint against excessive pronation. Attaching the strap end below the first metatarsal further greatly enhances the overall holding effect or retrograde stability of the apparatus. The point of attachment preferably is adjustable so that application of the forces exerted by the strap on the foot can be adjusted and controlled.

In addition, in order to allow for separate and independent adjustment of the tension applied by the strap to the arch of the foot, means are provided on the strap and the sleeve for releasably and adjustably fastening an intermediate portion of the strap to the first sleeve portion above the arch at about the first metatarsal. This provides an intermediate anchor point for the strap, so that the strap can be pulled relatively tightly around the heel without overtightening the tension on the arch, which could cause discomfort and possible cramping.

Other features of the present invention are the provision of additional means for releasably and adjustably fastening a second intermediate portion of the strap to the first sleeve portion at a location corresponding to the lateral side of the foot, after the strap has crossed over the second sleeve portion engaging the instep. The strap thus may be secured against riding up the instep and the heel onto the Achilles tendon during use. The means by which the first and second intermediate portions and the second end of the strap are fastened to the sleeve (or back onto the strap, as the case may be) preferably is achieved through opposing portions of fastening material for ease and comfort. To this end, the outer surface of the first sleeve portion may be made entirely of a fastening material so that the locations at which the intermediate and end portions of the strap fasten to the first sleeve portion can be most readily adjusted.

Hence it will be apparent that the improved apparatus of the present invention satisfies the desire for improvements in comfort, restraint of excessive pronation, assistance of resupination and holding effect or retrograde stability and, further, in a manner which retains the capability of self-application of the apparatus.

The above and other aspects and advantages of the invention will be apparent from the following detailed description taken in conjunction with the accompanying drawings.

BRIEF DESCRIPTION OF THE DRAWINGS

The accompanying drawings illustrate a presently preferred embodiment of the apparatus of the invention, in which.

DETAILED DESCRIPTION OF THE PREFERRED EMBODIMENT

Figure 1:
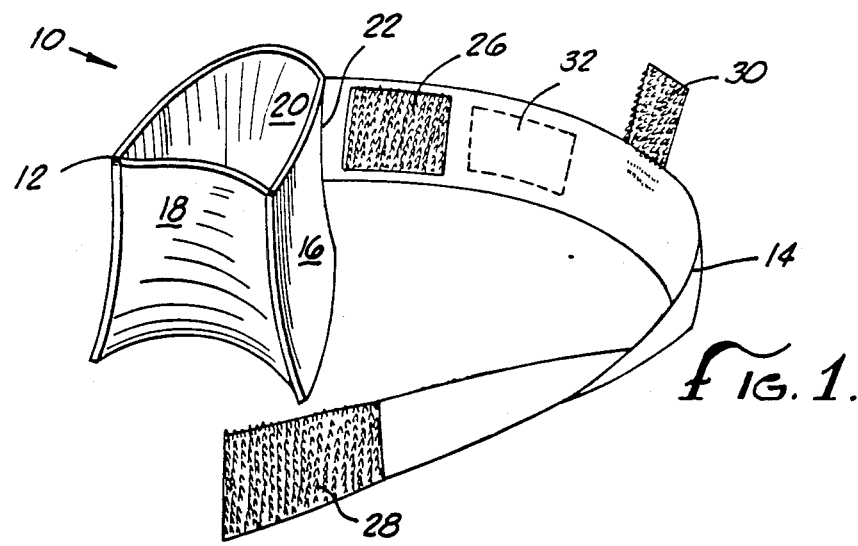
FIG. 1 is a perspective view of such apparatus showing its sleeve and strap.

As shown in the drawings for purposes of illustration, and particularly in FIG. 1 thereof, the present invention is embodied in an adjustable foot stabilization apparatus indicated generally by reference number 10, of which the principal components are a sleeve 12 and a strap 14, that can be applied to the foot for effectively resisting excessive pronation, assisting in resupination and providing retrograde stability of the foot. The cylindrical sleeve 12 is formed by an elongate and generally rectangular first sheet of material 16 secured by stitching or other means to a generally square second sheet of material 18. The rectangular or first sheet of material 16 has limited elasticity in both the circumferential and lateral directions. The square or second sheet of material 18 also has limited elasticity in the circumferential direction, but is substantially inelastic in the lateral direction. The first sheet of material 16 is formed of an elastic material backed on its exterior surface by a material having fastening properties, similar to that of VELCRO brand material, which can be fastened to opposing fastening material. A suitable material is available under the brand NYLATEX from Chattanooga Corporation. The second sheet of material 18 is formed of nylon elastic such as used in brassieres. The circumference and length of the sleeve can be preselected to provide different sizes to fit around the arch and instep of various size feet to provide a substantially snug fit which conforms to the shape of the foot.

The latex on the interior surface 20 of the sleeve 12 provides a gripping surface which extends almost completely around the back of the first sheet of material 16. The remaining inside of the sleeve is the back side of the second sheet of material 18. The gripping material serves to anchor the sleeve to the foot to provide a base from which the strap 14 can be pulled tight.

The strap 14 is elongated and has limited elasticity in the longitudinal direction. The strap 14 has one end 22 secured by stitching or other means to the first sheet 16 of the sleeve 12 at a location which will be at the lateral side approximately at the bottom of the foot (i.e., the lateral plantar location) when the sleeve is positioned around the arch of the foot. From this strap end 22, the strap 14 extends rearwardly of the foot toward the arch at an angle of approximately 20 degrees. The side of the strap 14 thus facing the first sheet 16 is provided with an arch adjustment portion 26 of opposing fastening material to the exterior surface of the first sheet and an outer end 28 of the strap, also of opposing fastening material. A tab 30 with an interior side of opposing fastening material extends outward from the strap 14 at approximately one-third of the distance from the secured end 22 to the outer end 28 of the strap. The outer side of the strap 14 is provided with an inelastic pad 32 (shown in phantom only in FIG. 1) located between the arch adjustment portion 26 and the tab 30. Except for the pad 32 and the opposite side of the strap end 28, the outer side of the strap 14 is formed of material with fastening properties similar to the exterior surface of the first sheet of material 16 of the sleeve 12. In the presently preferred embodiment, the strap 14 is made from an elastic VELCRO fastener material, Part No. 195521, supplied by Velcro U.S.A., Inc. of Manchester, N.H.

Figure 2:
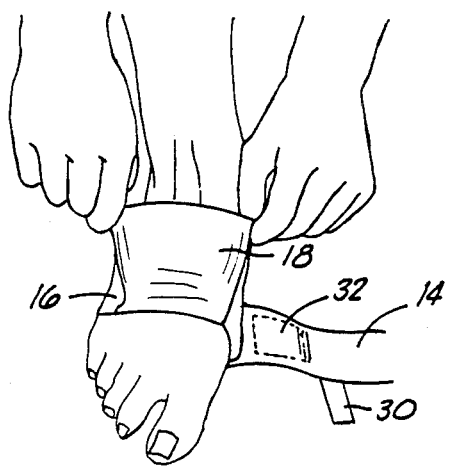
FIG. 2 is a perspective view illustrating the first step for applying such apparatus to a person's foot.

As shown in FIG. 2, the apparatus of the present invention is applied to the foot by first sliding the sleeve 12 over the foot and around the arch and instep. The second sheet of material 18 thus is over the instep while the first sheet of material 16 stretches to fit comfortably but snuggly around the arch and plantar portions of the foot. The strap 14 is angled slightly toward the heel of the foot with the tab 30, toward the front of the foot.

Figure 3:
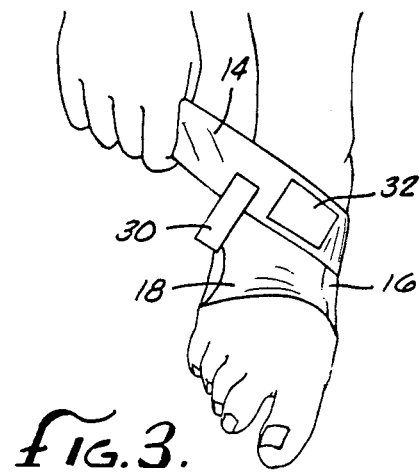
FIG. 3 is a perspective view of the second step for applying such apparatus to a person's foot.

Referring to FIG. 3, the strap 14, having been wrapped obliquely across the bottom of the foot and obliquely up and over the arch, is further wrapped across the instep. The arch adjustment portion 26 fastens to the exterior surface of the first sheet of material 16, with the inelastic pad 32 positioned over the instep of the foot. The pad 32 helps avoid binding action of the strap 14 on the instep.

Figure 4:
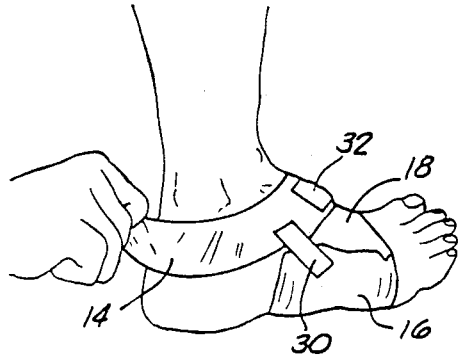
FIG. 4 is a perspective view of the third step for applying such apparatus to a person's foot.
Figure 5:
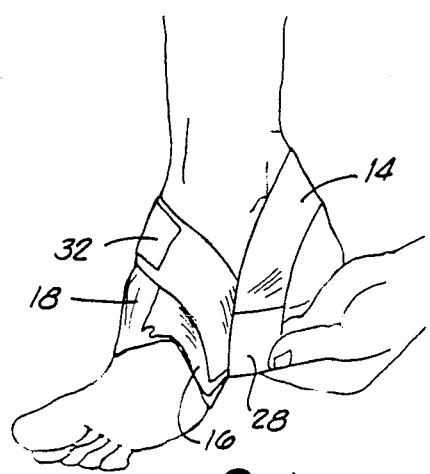
FIG. 5 is a perspective view of the fourth and final step for applying such apparatus to a person's foot.

As shown in FIG. 4, the strap 14 next is wrapped around the heel. The strap 14 is then wrapped back down the medial side of the foot as shown in FIG. 5. The outer end 28 of the strap 14 connects by the use of opposing fastening material to an anchor point on the first sheet of material 16 of the sleeve 12 below the level of the first metatarsal of the foot. In the preferred embodiment, the tab 30 is then fastened to the exterior surface of the first sheet of material 16. The tab 30 holds the strap from sliding up the ankle at the front of the foot and holds the strap from sliding up the heel bone to the Achilles tendon at the back of the foot.

The opposing fastening material on the arch adjustment portion 26 allows the tension of the strap 14 to be independently adjusted over the arch as the strap is fastened to the exterior surface of the first sheet 16 of the sleeve 12. With the aid of the gripping material 20 on the interior of the sleeve 12 and the arch adjustment portion 26, which is fastened adjacent to the laterally inelastic second sheet 18, the strap 14 is anchored firmly in place to prevent excessive pronation, assist in resupination and help provide retrograde stability.

As mentioned above, pronation and supination can be accurately described only in the three conventional anatomical planes (the sagittal, frontal and transverse planes), primarily with reference to the subtalar joint. By way of background, pivotal movement of the foot in the sagittal plane is termed dorsi flexion (upward movement of the front of the foot) or plantar flexion (downward movement). In the frontal plane, eversion is a pivotal movement of the bottom of the foot away from the midline of the body, while inversion is movement towards the midline. Finally, in the transverse plane abduction is defined as a pivotal movement of the front of the foot away from the midline of the body and adduction is movement toward the midline.

The foot is normally in a supinated position upon heel contact with the ground and pronates from heel contact through about the first half of the mid-stance phase of a gait cycle. In the pronated position the foot tends to be abducted, everted and dorsi flexed. In other words, the front of the foot is flexed upwardly and turned outwardly, while the bottom of the foot is rolled away from the midline of the body. During the last half of the mid-stance phase and as contact comes up to the toes for push-off, the foot is normally supinated, i.e., the front of the foot is flexed downwardly and turned inwardly, with the bottom of the foot rolled toward the midline.

To prevent excess pronation with the apparatus of the present invention, the foot is held in a position of slight inward turn and upward roll as the strap 14 is pulled tightly around the foot and fastened to the sleeve 12. Then, while walking or running, as the heel contacts the ground the strap 14 exerts resistive forces tending to prevent the foot from excessively pronating. The strap restrains the arch region of the foot so that the arch does not flex downwardly, and so that the bottom of the foot does not excessively roll away from the midline of the body. Significantly, the anchor point of the outer end 28 of the strap 14 is below the level of the first metatarsal on the foot. This anchor point causes the angle of the strap relative to the axis of motion of the foot to be transverse to the forces, rather than parallel, and thus to better resist those forces.

The portion of the strap 14 extending between the lateral plantar location 22 on the first sheet 16 of the sleeve 12 and the heel tends to support the arch joints from coming down and pulls up to prevent the foot from collapsing. The portion of the strap 14 extending from the ankle to the connection below the first metatarsal resists the front part of the foot from turning outwardly. During pronation, the strap 14 first pulls up on the arch to resist lengthening and spreading of the foot and then pulls on the foot to resist outward turning. When the foot hits the ground, the sleeve 12 will resist foot spreading, while stretching somewhat, and as foot contact progresses to the toes and the foot is lifted off the ground, the sleeve and strap will maintain the foot in proper position.

The combined actions of the sleeve and strap throughout the phases of the gait cycle, as thus described, serve to control foot motions relative to the subtalar joint. As a result, problems associated with excessive pronation are greatly diminished.

While a particular form of the invention has been illustrated and described, it will be apparent that various modifications can be made without departing from the spirit and scope of the invention. Accordingly, it is not intended that the invention be limited, except as by the appended claims.

We claim:

1. Improved apparatus for stabilizing the foot to control gait, comprising:
    a flexible sleeve for encircling the arch and instep of a person's foot consisting of a first sleeve portion adjoining at its opposite ends with the respective opposite ends of a second sleeve portion, said first sleeve portion of an extent to engage the plantar and arch portions of the foot and having limited elasticity in both the circumferential and lateral directions, and said second sleeve portion of an extent to engage the instep portion of the foot and having limited elasticity in the circumferential direction, said second sleeve portion being substantially inelastic in the lateral direction;
    gripping means on the inside surface of said sleeve for gripping the foot and anchoring said sleeve thereto;
    a flexible elongated strap having a first end connected to said first sleeve portion at about the lateral plantar location on the foot with the strap directed toward the arch, said strap of sufficient length to extend up and over the arch, across the instep, around the heel and back to the arch region;
    arch tension adjustment means for adjustably and releasably fastening an intermediate portion of said strap to said first sleeve portion above the arch at about the first metatarsal; and
    strap end fastening means for adjustably and releasably fastening a second end of said strap back near the arch after said strap has been wrapped across the instep and around the heel,
    said strap being sufficiently inelastic in the longitudinal direction to exert resistive forces to prevent excessive pronation and provide retrograde stability of the foot, while having limited elasticity to assist in resupination thereof.

2. Apparatus as set forth in claim 1, wherein said strap is fixed at a rearward angle of approximately 20 degrees to said sleeve at said first end of said strap.

3. Apparatus as set forth in claim 1, wherein said strap end fastening means is adapted for fastening said second end of said strap below the first metatarsal of the foot.

4. Apparatus as set forth in claim 3, wherein said strap end fastening means includes means for fastening said second end of said strap back onto said strap at a location between said first end of said strap and said intermediate portion of said strap below the first metatarsal.

5. Apparatus as set forth in claim 1, wherein said strap has a substantially inelastic portion located to overlie the instep.

6. Apparatus as set forth in claim 1, wherein said arch tension adjustment means and said strap end fastening means consist of opposing portions of fastening material.

7. Apparatus as set forth in claim 6, wherein one portion of said opposing portions of fastening material comprises the outer surface of said first sleeve portion.

8. Apparatus as set forth in claim 1, and further including means for adjustably and releasably fastening a second intermediate portion of said strap to said first sleeve portion at a location corresponding to the lateral side of the foot, after said strap has crossed over said second sleeve portion engaging the instep.

9. Apparatus as set forth in claim 8, wherein said means for fastening said second intermediate portion of said strap to said first sleeve portion includes a flexible tab extending from said strap, said tab and said first sleeve portion including opposing portions of fastening material.

10. Improved apparatus for stabilizing the foot to control gait, comprising:
    a flexible sleeve for encircling the arch and instep of a person's foot consisting of a first sleeve portion adjoining at its opposite ends with the respective opposite ends of a second sleeve portion, said first sleeve portion of an extent to engage the plantar and arch portions of the foot and having limited elasticity in both the circumferential and lateral directions, and said second sleeve portion of an extent to engage the instep portion of the foot and having limited elasticity in the circumferential direction, said second sleeve portion being substantially inelastic in the lateral direction;
    gripping means on the inside surface of said sleeve for gripping the foot and anchoring said sleeve thereto;
    a flexible elongated strap having a first end connected to said first sleeve portion at about the lateral plantar location on the foot with the strap directed at a rearward angle of approximately 20 degrees toward the arch, said strap of sufficient length to extend up and over the arch, across the instep, around the heel and back to the arch region; and
    strap end fastening means for adjustably and releasably fastening a second end of said strap at the arch below the first metatarsal of the foot after said strap has been wrapped across the instep and around the heel,
    said strap being sufficiently inelastic in the longitudinal direction to exert resistive forces to prevent excessive pronation and provide retrograde stability of the foot, while having limited elasticity to assist in resupination thereof.

11. Apparatus as set forth in claim 10, wherein said strap end fastening means includes means for fastening said second end of said strap back onto said strap at a location between said first end of said strap and an intermediate portion of said strap below the first metatarsal.

12. Apparatus as set forth in claim 11, wherein said strap has a substantially inelastic portion located to overlie the instep.

13. Apparatus as set forth in claim 10, and further including arch tension adjustment means for adjustably and releasably fastening an intermediate portion of said strap to said first sleeve portion above the arch at about the first metatarsal.

14. Apparatus as set forth in claim 13, wherein said arch tension adjustment means and said strap end fastening means consist of opposing portions of fastening material.

15. Apparatus as set forth in claim 10, and further including means for fastening a second intermediate portion of said strap to said first sleeve portion, said means including a flexible tab extending from said strap, said tab and said first sleeve portion including opposing portions of fastening material.

16. Apparatus as set forth in claim 9 wherein said strap end fastening means comprises the outer surface of said first sleeve portion formed of one fastening material and the second end of said strap having an opposite fastening material.

17. Improved apparatus for stabilizing the foot to control gait, comprising:
a sleeve for encircling the arch and instep of a person's foot consisting of a first sheet of flexible fastening material joined at its opposite ends to the respective opposite ends of a second sheet of flexible material, said first sheet of material of an extent to engage the plantar and arch portions of the foot and having limited elasticity in both the circumferential and lateral directions, and said second sheet of material of an extent to engage the instep portion of the foot and having limited elasticity in the circumferential direction, said second sheet of material being substantially inelastic in the lateral direction;
gripping means on the inside surface of said sleeve for gripping the foot and anchoring said sleeve thereto;
a flexible elongated strap having a first end connected to said first sheet of material at about the lateral plantar location on the foot with the strap directed at a rearward angle of approximately 20 degrees toward the arch, said strap of sufficient length to extend up and over the arch, across the instep, around the heel and back to the arch region,
said strap formed of fastening material on the side opposite said sleeve,
said strap further having an intermediate portion of fastening material on the side facing said sleeve for adjustably and releasably fastening said intermediate portion of said strap to said first sleeve portion above the arch at about the first metatarsal,
said strap further having a portion of fastening material on the side facing said sleeve for adjustably and releasably fastening a second end of said strap selectively to said first sheet of material of said sleeve or back onto said strap at the arch below the first metatarsal of the foot after said strap has been wrapped across the instep and around the heel,
said strap being sufficiently inelastic in the longitudinal direction to exert resistive forces to prevent excessive pronation and provide retrograde stability of the foot, while having limited elasticity to assist in resupination thereof.

18. Apparatus as set forth in claim 17, wherein said strap has a substantially inelastic portion formed therein to overlie the instep.

19. Apparatus as set forth in claim 17, and further including a tab of flexible material extending from said strap at a location corresponding to the lateral side of the foot for adjustably and releasably fastening a second intermediate portion of said strap to said first sheet of material, after said strap has crossed said second sheet of material engaging the instep, said tab having fastening material on the side facing said first sheet of material.

* * * * *